United States Patent [19]

Luh et al.

[11] Patent Number: 4,873,365
[45] Date of Patent: Oct. 10, 1989

[54] PROCESS FOR THE PREPARATION OF ISOPHORONE DIISOCYANATE FROM ISOPHORONE DICARBAMYL ESTERS USING HIGHLY SELECTIVE SNO₂ OR CUO CATALYSTS

[75] Inventors: Yuhshi Luh, Orange; Peter S. Forgione, Stamford, both of Conn.

[73] Assignee: American Cyanamid Company, Stamford, Conn.

[21] Appl. No.: 848,417

[22] Filed: Apr. 4, 1986

[51] Int. Cl.⁴ .......................................... C07C 119/00
[52] U.S. Cl. .................................................. 560/345
[58] Field of Search ........................................ 560/345

[56] References Cited

FOREIGN PATENT DOCUMENTS 158747 9/1982 Japan.

Primary Examiner—Alan Siegel
Attorney, Agent, or Firm—Roger S. Benjamin

[57] ABSTRACT

Isophorone diisocyanate, 3-isocyanatomethyl-3,5,5-trimethylcyclohexylisocyanate (IPDI) is prepared by liquid phase thermolysis of the corresponding bis-carbamic acid ester into the corresponding isocyanate and alcohol, respectively, in the presence of a highly selective metal oxide catalyst ($SnO_2$ and/or $CuO$). Typically, the cracking reaction is carried out at a temperature from 225° to 350° C., at a pressure of from 20 to 50 mm Hg. These catalysts give high IPDI yields with high conversions of the carbamic acid esters.

9 Claims, No Drawings

PROCESS FOR THE PREPARATION OF ISOPHORONE DIISOCYANATE FROM ISOPHORONE DICARBAMYL ESTERS USING HIGHLY SELECTIVE SNO₂ OR CUO CATALYSTS

The present invention relates to an improved process for the preparation of isocyanates from carbamic acid esters. More particularly, it pertains to the preparation of isophorone diisocyanate by the liquid phase thermolysis of isophorone dicarbamyl esters using highly selective $SnO_2$ and/or $CuO$ catalysts.

BACKGROUND OF THE INVENTION

Diisocyanates are a known useful class of compounds. They are reactive with active hydrogen-containing compounds such as polyhydroxy compounds to produce polyurethanes and polyamido compounds to produce polyureas. Such reaction products are useful for protective and decorative coatings, for making molded and extruded articles, such as surgical tubings, and for many other purposes.

Special mention is made of a particularly useful family of diisocyanates: the 3-(isocyanatomethyl)-3,5,5-trilower-alkyl cyclohexylisocyanates. These are distinguished by their excellent applicability for cross-linking reactions of proteinaceous materials (tanning agents), and further for example by their superior adhesive properties in the bonding of metals with high-molecular weight synthetic or natural substances as, for example, the bonding of metals with high-molecular weight synthetic or natural substances as, for example, the bonding of metals to various types of rubbers. They are particularly well suited for use in reaction injection molding (RIM) compositions. A diisocyanate particularly effective carries methyl substituents in the 3-, 3- and 5-positions and is known as isophorone diisocyanate (IPDI).

IPDI (isophorone diisocyanate) has been prepared by a number of routes.

In Schmitt et al., U.S. Pat. No. 3,401,190, isophorone diamine (IPDA), also known as 3-(aminomethyl)-3,5,5-tri-methylcyclohexylamine-(1), is reacted with phosgene at 100° C. for 28 hours and the by-product hydrogen chloride and excess phosgene are removed by blowing nitrogen through the liquid reaction mixture, then the product is recovered by vacuum distillation. Drawbacks of this process are the toxicity of the phosgene and corrosion problems associated with by-product HCl.

The difficulties with direct phosgenations have led to the development of non-phosgenation routes, and these generally involve the pyrolytic thermolysis or cracking of a carbamic acid ester of the formula:

$R^1(NH-CO-OR^2)_n$ in which $R^1$ is an aliphatic or aromatic radical of the type obtained by removal of the isocyanate groups from, for example isophorone diisocyanate (IPDI) or 2,4′ and/or 4,4-diisocyanato diphenyl methane (MDI), $R^2$ is usually a primary or secondary aliphatic hydrocarbon radical of from 1 to 4 carbon atoms and n is 2 or an integer of greater than 2.

In general, the prior art cracking reactions are carried out in the vapor phase or in the liquid phase, with or without accelerators, or catalysts or other additives, generally called auxiliaries. It is a general rule also that both aromatic isocyanates (such as MDI) and aliphatic isocyanates (such as IPDI) are produced under the same general conditions and influenced in the same way by the modifiers and/or promoters employed and, therefore any catalyst useful for one would be expected to be useful for the other.

Merely by way of illustration, Merger et al., U.S. Pat. No. 4,482,499 disclose that urethanes, including IPDU, will be thermally cleaved to isocyanates at temperatures in the range of 175° C. to 600° C. in the presence of carbon, preferably in an agitated carbon bed or in a fluidized bed containing carbon. The drawbacks of this basically gas phase process are that it requires high energy input, produces a lower product output per unit operation time, gives a low IPDU conversion and a moderate IPDI yield, and requires a high b.p. solvent for separation of product. Hellbach et al., European Patent Application No. 126300 A1 (Apr. 17, 1984) prepared IPDI by passing IPDU through a cracker which was packed with brass rings at an average temperature of 410° C. This is considered to be in a gaseous phase, and the drawbacks include the high temperature (high energy) operation, and lower product output per operation time unit. Engbert et al., European Patent Application No. 0092738A1 (Apr. 14, 1983) prepared IPDI and other diisocyanates by cracking IPDU and other carbamic acid esters in a liquid phase, continuous process at a temperature of 150°–450° C., pressure 0.01–20 bar, using a soluble catalyst, e.g., dibutyltin dilaurate, and a high b.p. chlorinated solvent. Drawbacks of this process include a low IPDU conversion and low IPDI yields, requiring a high b.p. solvent as a medium, potential need for make-up for solvent loss, and potential hazards of using chlorinated aromatics as solvent. Sunderman et al., U.S. Pat. No. 4,388,246, prepared IPDI and other diisocyanates from IPDU and other carbamic acid esters by cracking in a liquid phase at a temperature of 150°–350° C. and a pressure of 0.001–20 bar in the presence of auxiliary agents (HCl, organic acid chlorides, organotin (IV) chlorides, etc.). Solvents and catalysts may also be employed. Drawbacks include the requirements that the auxiliary agents are basically chlorides, which may contaminate the final isocyanate product, the loss and make-up of the auxiliary agents which is costly, and the fact chlorides are acidic and therefore cause serious corrosion problems. Moreover, the high vacuum, approximately 4 mm Hg, cannot easily be achieved in industrial operations. Spohn, U.K. Patent Publication No. 2,113,673A (Aug. 10, 1983) describes the production of aromatic isocyanates (not aliphatic) by liquid thermolysis at atmospheric pressure or above (not sub-atmospheric) in the presence of a catalyst containing Ti, Sb, Zr or Sn. The organic soluble tin compounds employed did not include tin oxide. Mitsubishi, Japanese Patent Pubication No. 54-88201 (July 13, 1979) discloses the use of compounds from alkaline earth metals (Be, Mg, Ca, Ba, Sr, Ra) for cracking of urethanes to isocyanates. No mention is made of $SnO_2$, $CuO$ as cracking catalysts. Moreover, experiments have shown that oxides of alkaline earth metals (BeO, MgO, CaO, SrO, RaO) give low IPDI yields (see infra). The only examples in this Japanese publication make toluenediisocyanate (TDI), an aromatic compound, and, in general, only low TDI yields were obtained Asahi Kasei, Japanese Patent Publication 57-158747 (Sept. 30, 1982) discloses the use of numerous metal oxides (Zn, Cu, Au, Ag, Cd, Al, Ga, In, Ge, Ti, Zr, Sn, etc.) as cracking catalysts. Also mentioned, but not exemplified, is the use of IPDU and other aliphatic urethanes as substrates. It is claimed that all metal oxides are effective cracking catalysts. In the examples, however, only aromatic urethanes, e.g., MDU are employed, and many of the oxides used are better than $SnO_2$ and CuO in terms of MDI yields obtained.

It has now unexpectedly been discovered and is the subject matter of this invention that $SnO_2$ and CuO are clearly superior to all other known metal oxide catalysts when used for the thermal pyrolysis of IPDU to IPDI. In the present invention, $SnO_2$ and CuO as catalysts give high IPDI yields. In contrast, use of other metal oxides, many of which are substantially superior to $SnO_2$ and CuO when used with an aromatic substrate, e.g., MDI, actually give lower IPDI yields (5–55%).

The present invention is based on the discovery of two highly specific and selective metal oxide catalysts, $SnO_2$ and CuO, from many metal oxide catalysts recommended in the prior art. A systematic study has found that these two catalysts are especially attractive for converting isophorone diurethanes to isophorone diisocyanate because they afford IPDI in high selectivity and yield little residual undesired products such as isocyanurate, carbodiimide and other side products. They are suitable for low temperature, liquid phase processes. Low catalyst loadings are required The catalysts are easily recycled, and there are no specific requirements either for solvents or auxiliary agents, as in some of the prior art. Sub-atmospheric pressures (30–45 mm Hg) are suitable, and these can be easily generated by conventional aspiration equipment. Savings on reactor size are achievable because solvent is not required The catalysts, which are insoluble solids, are easily separated from the products. Although the invention is primarily directed to cracking IPDU (methyl or butyl carbamates) to IPDI, the technology is extendable to other pyrolytic cracking reactions involving alkyl carbamic acid esters attached to aliphatic and cycloaliphatic substituents, for example, the cracking of $\alpha,\alpha,\alpha',\alpha'$-tetramethylxylylene diurethane (TMXDU) methyl or butyl ester to $\alpha,\alpha, \alpha', \alpha'$-tetramethylxylylene diisocyanate (TMXDI).

SUMMARY OF THE INVENTION

According to the present invention, in a process for the preparation of isophorone diisocyanate by cleaving a corresponding carbamic acid ester at temperatures of 175° C. to 400° C. in the presence of a metal oxide, there is provided the improvement which comprises using $SnO_2$ or CuO or a mixture thereof as the catalyst.

In preferred features of the invention, the reaction will be carried out at a temperature in the range of from about 225° C. to about 350° C. The pressure used preferably is in the range of from about 10 to about 50 mm Hg. The amount of catalyst preferably is in the range of from about 0.1 to about 15 wt. % based on the weight of the carbamic acid ester used. Preferably the carbamic acid ester used is the methyl ester or the butyl ester, although esters of from 1 to 4 carbon atoms can be used.

DETAILED DESCRIPTION OF THE INVENTION

The isophorone diurethane used as a starting material can be made in known ways. Isophorone can be reacted with hydrocyanic acid followed by hydrogenation of the resultant dinitrile to the corresponding diamine. This reaction has been described in U.S. Pat. Nos. 3,270,044 and 3,352,913. The diamine can be converted to the carbamic acid ester

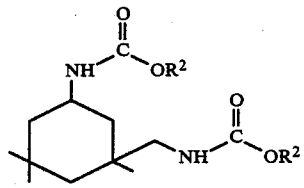

wherein $R^2$ is as above defined, e.g., $C_1$–$C_4$ alkyl, by methods known to those in the art. In one such process, the diamine is reacted with a chloroformic acid alkyl ester. Other processes to make the carbamates are carbonylation of the corresponding nitro or amino compounds in the presence of an alcohol; or condensation of the carbamic acid esters with formaldehyde or other aldehydes or ketones. The diamine can also be reacted with urea and alcohols. In Heitkamper et al., U.S. Pat. No. 4,388,238, Example 9, isophorone diamine, n-butylcarbamate and butanol are co-reacted for 4 hours at 180° C. and high yields of the isophorone n-butyl carbamic acid diester are obtained. In any event, the suitability of carbamic acid esters for the process of the present invention does not depend upon the method of production.

The polyurethanes are thermally cleaved in the gas phase or in the liquid phase, preferably the latter. In the gas phase, the temperatures will be in the range of 300° C. to 600° C. In the liquid phase, cleaving is preferably at 175° C. to 350° C. Although a solvent can be used, such as a high boiling aromatic hydrocarbon, it is preferred not to use a solvent. The catalysts preferably should have a large surface area being, for example, in the form of powders or granules, having average diameters of 1 to 10 millimeters. The catalysts may be used in various arrangements. They can be used in fixed beds, for instance, by charging variously shaped reactors, such as tube, tank, boiler or fluidized bed type reactors, with catalyst granules, pellets, or other shapes, so that the urethane to be pyrolytically decomposed can be continuously directed through a fixed bed of catalyst. Alternatively, and preferably, however, the catalyst may be suspended in a mixing reactor.

Cleavage may be by a batch type method or on a continuous basis under reduced, normal or increased pressure. The cleaving and separating of the products by distillation of the alcohol, possibly the diisocyanate and any partially reacted monoisocyanate and any unreacted diurethane, and/or optional solvent can take place simultaneously or in a sequence. With simultaneous cleaving and separation in the liquid phase, a temperature-pressure ratio is advantageously chosen which corresponds to the boiling point of the low boiling component of the bottom fraction. As a result of a number of experiments, for a batch type process, without a solvent, the cracking reaction is preferably carried out at a temperature of from 225° to 350° C., most preferably at 235°–260° C., at a pressure of 20 to 50 mm Hg, most preferably at 35–45 mm Hg, the presence of from 0.1 to 6 wt. %, most preferably, about 0.5 to 3.0 wt. % selective metal oxide catalyst, $SnO_2$ or CuO, based on IPDU. The reaction times will vary, but usually from about 2 to about 6 hours are sufficient. The progress of the reaction can be followed in a number of ways, e.g., by measuring the alcohol amount evolved, or by analyzing aliquots of the reaction mixture as a function of time, e.g., by means of a gas chromatograph.

The product can be recovered in ways known to those skilled in this art. Distillation is preferred, because it boils at 126°–128° C. under a 2 mm Hg vacuum and at 158°–159° C. under a 15 mm Hg vacuum.

DESCRIPTION OF THE PREFERRED EMBODIMENTS

The following examples illustrate the processes of the present invention and provide data to show their advantages over the prior art. They are not to be construed to limit the claims in any manner whatsoever.

In the following Examples and Tables the following abbreviations are used:

IPDU—3-(methoxycarbonylaminomethyl)-3,5,5-trimethyl-1-(methoxycarbonylamino)-cyclohexane;

IPDI—3-(isocyanatomethyl)-3,5,5-trimethylcyclohexylisocyanate; and

IPUI—3-(isocyanato(or methoxycarbonylamino)methyl)-3,5,5-trimethyl-1-(methoxycarbonylamino-(or isocyanato))-cyclohexane.

EXAMPLE 1

This provides a general method for cracking isophorone diurethane (IPDU) to isophorone diisocyanate (IPDI).

A reaction mixture containing 20 g of isophorone dimethylurethane and 0.1 g of $SnO_2$ (0.5 wt. % of isophorone dimethylurethane charged) is heated to 235°–245° C. for 4 hours at a constant pressure of 35–40 mm Hg using a pressure regulator. The reaction vessel is connected in sequence to an air-cooled condenser with a receiving flask connected to an acetone-dry ice cooled trap. After reaction, the acetone-drying trap is found to contain 4.0 g of methanol (90% of theoretical yield). The reaction products in the pot and the air-cooled receiver are analyzed by means of gas chromatograph using an internal standard method. It is found that 10.1 g of isophorone diisocyanates (65% of theoretical yield) and 4.8 g of isophorone monoisocyanates (27% of theoretical yield) are formed; 95% of isophorone diurethane was converted.

EXAMPLES 2 and 3

The general procedure of Example 1 is repeated in separate reactions employing the specified catalysts, $SnO_2$ and CuO, respectively, and reaction conditions. For comparison purposes, 20 metal oxides of the prior art are also used. The conditions employed and the results obtained are set forth in Table 1, yields being expressed in percent (%):

TABLE 1
LIQUID PHASE CRACKING OF IPDU (METHYL) TO IPDI

| EXAMPLE | CATALYST | g CATALYST/g IPDU | TEMP (°C.) | PRESSURE (mm Hg) | IPDI YIELD | IPUI YIELD | IPDI & IPUI YIELD | IPDU CONVERSION | MEOH YIELD | RUN TIME (MIN) | IPDI/IPUI | (IPDI & IPUI) SELECTIVITY, % |
|---|---|---|---|---|---|---|---|---|---|---|---|---|
| 2 | $SnO_2$ | 0.05 | 235 | 30 | 81 | 12 | 93 | 97 | 95 | 45 | 6.75 | 96 |
| 3 | CuO | 0.05 | 235 | 30 | 74 | 19 | 93 | 98 | 92 | 45 | 3.89 | 95 |
| A | $Ga_2O_3$ | 0.05 | 235 | 30 | 24 | 33 | 57 | 88 | 64 | 45 | 0.73 | 65 |
| B | $ZrO_2$ | 0.03 | 240 | 30 | 9 | 47 | 56 | 60 | 31 | 45 | 0.19 | 93 |
| C | $Fe_2O_3$ | 0.03 | 233 | 30 | 46 | 9 | 55 | 99 | 97 | 45 | 5.11 | 55 |
| D | CoO | 0.05 | 235 | 30 | 35 | 20 | 55 | 95 | 91 | 45 | 1.75 | 58 |
| E | ZnO | 0.05 | 235 | 30 | 36 | 16 | 52 | 94 | 70 | 45 | 2.00 | 55 |
| F | NiO | 0.05 | 235 | 30 | 9 | 39 | 48 | 65 | 33 | 45 | 0.23 | 74 |
| G | $SiO_2$ | 0.05 | 235 | 30 | 16 | 25 | 41 | 90 | 62 | 45 | 0.64 | 46 |
| H | MnO | 0.05 | 235 | 30 | 5 | 33 | 38 | 75 | 36 | 45 | 0.15 | 51 |
| I | $CeO_2$ | 0.03 | 235 | 30 | 12 | 20 | 32 | 92 | 71 | 45 | 0.60 | 35 |
| J (basic) | $Al_2O_3$ | 0.05 | 235 | 30 | 6 | 16 | 22 | 88 | 44 | 45 | 0.38 | 25 |
| K | BaO | 0.05 | 225 | 30 | 10 | 8 | 18 | 97 | 78 | 30 | 1.25 | 19 |
| L (neutral) | $Al_2O_3$ | 0.05 | 235 | 30 | 7 | 10 | 17 | 96 | 68 | 45 | 0.70 | 18 |
| M | $SeO_2$ | 0.05 | 235 | 30 | 1 | 14 | 15 | 56 | 15 | 45 | 0.07 | 27 |
| N | $PbO_2$ | 0.05 | 220 | 30 | 6 | 4 | 10 | 97 | 77 | 30 | 1.50 | 10 |
| O (acidic) | $Al_2O_3$ | 0.05 | 235 | 30 | 2 | 7 | 9 | 93 | 64 | 45 | 0.33 | 04 |
| P | CaO | 0.05 | 235 | 30 | 3 | 5 | 8 | 95 | 85 | 45 | 0.60 | 08 |
| Q | SrO | 0.05 | 235 | 30 | 2 | 4 | 6 | 96 | 78 | 45 | 0.50 | 06 |
| R | $TiO_2$ | 0.05 | 235 | 30 | 1 | 3 | 4 | 93 | 64 | 45 | 0.33 | 04 |
| S | $TiO_2$ | 0.05 | 235 | 30 | 1 | 3 | 4 | 93 | 64 | 45 | 0.33 | 04 |
| T | $WO_3$ | 0.05 | 233 | 30 | 1 | 3 | 4 | 96 | 76 | 45 | 0.33 | 05 |

The data in Table 1 indicate that although the prior art indicates that using metal oxides for thermal cracking of urethane to isocyanates is feasible, two oxide catalysts are far superior, and these are the $SnO_2$ and CuO catalysts of Examples 1-3, when an isophorone diurethane is the substrate. Yields of 81 and 74% of IPDI containing 12% and 19% of IPUI were obtained with $SnO_2$ and CuO in Examples 2 and 3, respectively, but yields ranging only from 1% to 46% were obtained with the catalysts in Comparative Examples A–T, respectively. Moreover, these results are unexpected in view of the data in the prior art, particularly that in Japanese Patent Publication No. 57-158747. Using diphenylmethane diurethane as a substrate, $SiO_2$, especially, and numerous other oxides were, in fact, superior to either of CuO and $SnO_2$, just the opposite of what was found herein, with isophorone diurethane as a substrate.

IPUI. Overall, 88.2% of the IPDU is converted. Total material recovery is 95.9% based on starting IPDU.

EXAMPLES 7–12

The general procedure of Example 1 is repeated, making changes in the ester employed, the catalyst, reaction time, and reaction pressure. The materials used and the results obtained are set forth in Table 2:

TABLE 2

| | | LIQUID PHASE CRACKING OF IPDU (DIBUTYL) TO IPDI | | | | | | |
|---|---|---|---|---|---|---|---|---|
| EXAMPLE | IPDU CHARGED | CATALYST AMOUNT | TEMP (°C.) | PRESSURE (mm Hg) | TIME (HRS) | IPDI YIELD, % | IPUI YIELD, % | IPDU CONVERSION, % |
| 7 | 5.0 g | $SnO_2$/ 0.1 g | 245–250 | 30 | 3.8 | 39 | 50 | 89 |
| 8 | 8 g | $SnO_2$/ 0.12 g | 235–255 | 35 | 2.5 | 43 | 47 | 90 |
| 9 | 8 g | $SnO_2$/ 0.08 g | 250–260 | 40 | 3.3 | 59 | 34 | 93 |
| 10 | 112 g | $SnO_2$/ 0.55 g | 250–260 | 40 | 10 | 46 | 24 | 75 |
| 11 | 22 g | $SnO_2$/ 0.2 g | 250–260 | 40 | 6 | 37 | 44 | 92 |
| 12 | 17 g | CuO/ 0.1 g | 250–260 | 35 | 7 | 49 | 37 | 96 |

EXAMPLE 4

Following the procedure of Example 1, 0.58 g of isophorone dibutylurethane and 0.01 g of $SnO_2$ catalyst are charged to the reaction flask, and heated at 265° C. for 10 minutes under a pressure of 35 mm Hg. At the end of this time, the reaction products are analyzed by gas chromatography using the internal standard method. Analysis indicates a 17.0% yield of IPDI (relative to charged IPDU) and a 51.8% yield of IPUI. Overall, 73.4% of the IPDU is converted. Total material recovery was 95.4 wt. % based on IPDU.

EXAMPLE 5

Following the procedure of Example 1, 0.52 g of isophorone dibutylurethane and 0.0805 g of $SnO_2$ catalyst are charged to the reactor at a temperature of 280° C. for 10 minutes under a pressure of 15 mm Hg. At the end of this time, the reaction products are analyzed by GC using the internal standard method. Analysis shows a 32.3% yield (relating to charged IPDU) of IPDI and a 49.8% yield of IPUI. Overall, 85.6% of IPDU is converted. Total material recovery is 96.5 wt. % based on IPDU.

EXAMPLE 6

Following the procedure of Example 1, 0.52 g of isophorone dibutylurethane and 0.0775 g of $SnO_2$ catalyst are heated at 280° C. for 15 minutes under 15 mm Hg of pressure. At the end of reaction, the reaction products are analyzed by gas chromatography using the internal standard method. Analysis shows a 40.4% yield (based on charged IPDU) of IPDI and a 43.7% yield of IPUI.

The above-mentioned patents and publications are incorporated herein by reference.

Many variations in the present invention will suggest themselves to those skilled in this art in light of the above, detailed description. For example, although batch processes have been described above, the invention is amenable to continuous cracking with the selective catalysts wherein conversions can be achieved in good yields in even shorter times, for example in the order of from 5 to 30 minutes. Kinetic studies have shown that with 3–15 wt % $SnO_2$ at 235°–280° C. at 15–35 mm Hg using IPDU butyl ester typically substantial (at least about 90%) conversion of the IPDU is obtained in only about 10 minutes. All such obvious variations are within the full intended scope of the appended claims.

We claim:

1. In a process for the preparation of isophorone diisocyanate by cleaving a corresponding biscarbamic acid ester at a temperature of 175° C. to 400° C. in the presence of a metal oxide catalyst, the improvement which comprises using $SnO_2$ or CuO or a mixture thereof as said catalyst to produce said isophorone diisocyanate with high selectivity and high yield.

2. A process as defined in claim 1 wherein the catalyst comprises $SnO_2$.

3. A process as defined in claim 1 wherein the catalyst comprises CuO.

4. A process as defined in claim 1 wherein the temperature used is from about 225° C. to about 350° C.

5. A process as defined in claim 1 wherein the pressure used is from about 10 to about 50 mm Hg.

6. A process as defined in claim 1 wherein the catalyst used is in the amount of from about 0.1 to about 15 wt. % based on the weigh of said bis-carbamic acid ester.

7. A process as defined in claim 1 wherein the bis-carbamic acid ester used is the methyl ester or the butyl ester.

8. A process as defined in claim 1 wherein the bis-carbamic acid ester used is the butyl ester.

9. A process as defined in claim 1 wherein the bis-carbamic acid ester used is the methyl ester.

* * * * *